United States Patent [19]
Elyasaf et al.

[11] Patent Number: 5,892,579
[45] Date of Patent: Apr. 6, 1999

[54] OPTICAL INSPECTION METHOD AND APPARATUS

[75] Inventors: Emanuel Elyasaf; Yair Eran, both of Rehovot, Israel

[73] Assignee: Orbot Instruments Ltd., Yavne, Israel

[21] Appl. No.: 843,453

[22] Filed: Apr. 16, 1997

[30] Foreign Application Priority Data

Jul. 16, 1996 [IL] Israel ........................................ 118872

[51] Int. Cl.$^6$ ................................................. G01N 21/88
[52] U.S. Cl. ..................... 356/239.8; 350/237.47
[58] Field of Search ................... 356/237, 394, 356/394.5, 237.2, 237.3, 237.4, 237.5, 239.7, 238.8

[56] References Cited

U.S. PATENT DOCUMENTS

| | | | |
|---|---|---|---|
| 4,449,818 | 5/1984 | Yamaguchi et al. | 356/237 |
| 4,669,885 | 6/1987 | Ina | 356/443 |
| 4,952,058 | 8/1990 | Noguchi et al. | 356/237 |
| 5,216,479 | 6/1993 | Dotan et al. | 356/73 |
| 5,235,400 | 8/1993 | Terasawa et al. | 356/237 |
| 5,495,337 | 2/1996 | Goshorn et al. | 356/376 |
| 5,563,702 | 10/1996 | Emery et al. | 356/73 |
| 5,572,598 | 11/1996 | Wihl et al. | 382/144 |
| 5,586,058 | 12/1996 | Aloni et al. | 364/552 |
| 5,619,429 | 4/1997 | Aloni et al. | 364/552 |

FOREIGN PATENT DOCUMENTS

| | | |
|---|---|---|
| 0 459 489 | 12/1991 | European Pat. Off. . |
| 532927 | 3/1993 | European Pat. Off. . |
| WO9602825 | 2/1996 | WIPO . |

*Primary Examiner*—Richard A. Rosenberger
*Attorney, Agent, or Firm*—Ladas & Parry

[57] ABSTRACT

This invention discloses an apparatus for optically inspecting an object having upper and lower faces for indicating the condition of the object, including a lighting system periodically reflecting a beam of light from one face of the object to produce a series of short-duration time-spaced reflected beams, and periodically transmitting a beam of light through both faces of the object to produce a series of short-duration time-spaced transmitted beams time-interlaced with the reflected beams, a sensor sensing the short-duration time-spaced reflected beams and transmitted beams, and generating electrical outputs corresponding thereto, and a processor receiving the electrical outputs and processing them to provide an indication of the condition of the object.

A method of optically inspecting an object having upper and lower faces for indicating the condition of the object is also described.

32 Claims, 3 Drawing Sheets

FIG. 4
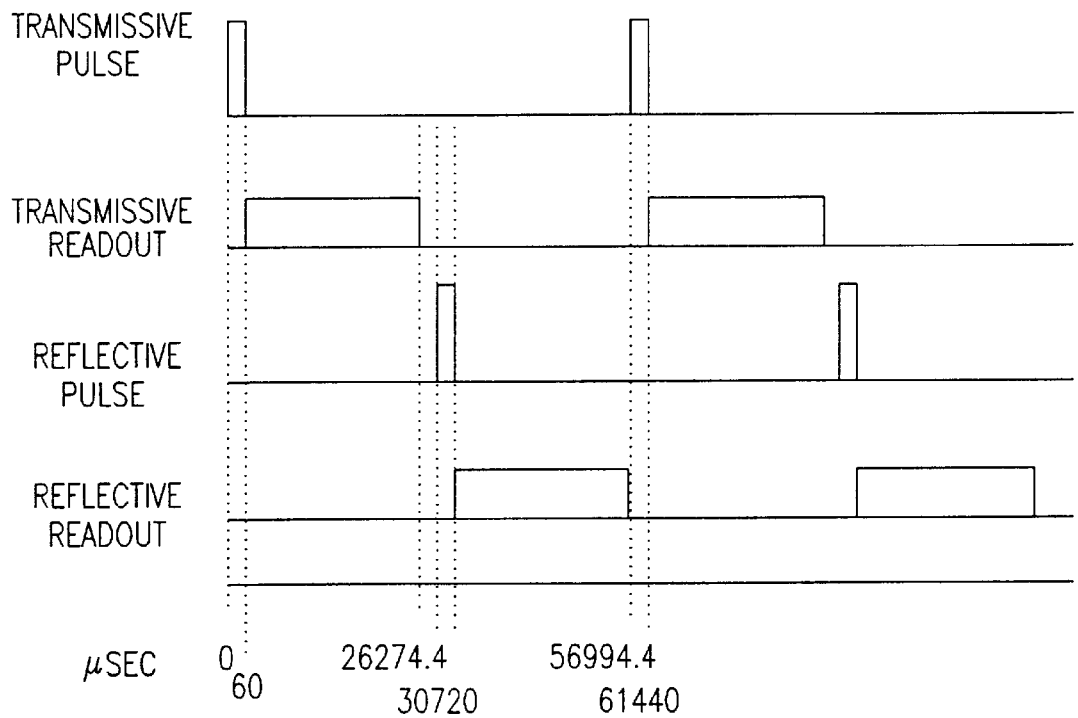
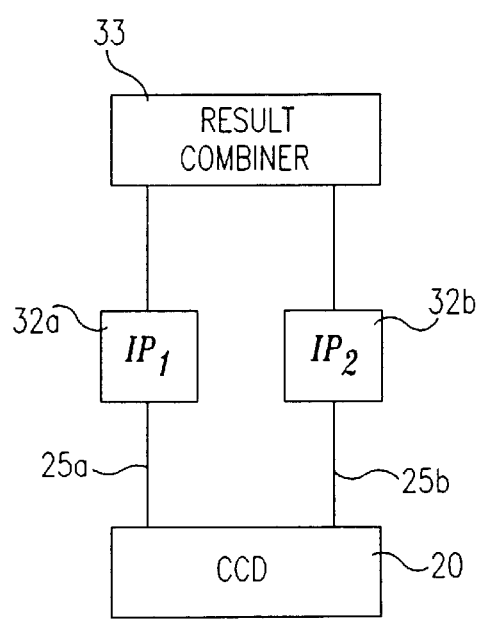
FIG. 5

5,892,579

OPTICAL INSPECTION METHOD AND APPARATUS

OPTICAL INSPECTION METHOD AND APPARATUS

The present invention relates to a method and apparatus for optically inspecting an object. The invention is particularly useful for optically inspecting a photomask having clear areas and opaque areas in order to detect the presence or absence of defects in both the clear areas and the opaque areas. The invention is therefore described below with respect to this application, but it will be appreciated that it could also be advantageously used in other applications, e.g., for inspecting other objects such as printed circuit boards, flat panel displays, etc.

BACKGROUND OF THE INVENTION

A large number of methods and systems are known for optically inspecting articles. For example, Dotan et al. U.S. Pat. No. 5,216,479 discloses a system for optically inspecting objects, particularly printed circuit boards, by projecting a beam of light onto one face of the object, and sensing reflected light reflected from that face and fluorescent light induced at that face, such sensed light being then used to indicate defects in the respective face of the object; the described system also transmits the light through the object and senses the transmitted light at the opposite face of the object for detecting defects in plated through-holes in the printed circuit board. Published European Patent Application 92114182.6 also discloses an optical inspection method and system utilizing both reflected light and transmitted light for detecting defects. The systems in both of the above patents are based on a scanning technique wherein the light beam, e.g., a laser beam, is caused to scan the object being inspected.

SUMMARY OF THE INVENTION

An object of the present invention is to provide a novel method and apparatus for optically inspecting an object by the use of both reflected beams and transmitted beams but having advantages over the method and system described in the above publications.

According to one aspect of the present invention, there is provided a method of optically inspecting an object having upper and lower faces for indicating the condition of the object, comprising: periodically reflecting a beam of light from one face of the object to produce a series of short-duration time-spaced reflected beams; periodically transmitting a beam of light through the object including both faces thereof to produce a series of short-duration time-spaced transmitted beams time-interlaced with the reflected beams; sensing the short-duration time-spaced reflected beams and transmitted beams, and generating electrical outputs corresponding thereto; and processing the electrical outputs to provide an indication of the condition of the object.

According to further features in the described preferred embodiments of the invention, the reflected beams and transmitted beams are sensed by an area-type image sensor. In addition, the reflected beams and transmitted beams are produced by a high-intensity light source periodically energized for periods of less than 1 millisecond, preferably less than 100 microseconds at a frequency of more than 1 MHz. In the preferred embodiments described below, the duration of each high-intensity light beam is about 60 microseconds, and the frequency is 40 MHz. Such an arrangement, as will be described below, permits "on the fly" optical inspection of the object, while the object is in continuous motion, without blurring the image.

Particularly good results are obtainable by using the CCD image sensor developed for the NASA Pluto Program. This sensor is a cooled back illumination CCD image sensor and has an enhanced quantum efficiency in the ultraviolet (UV) spectral range. It has, as well, a very high data rate and very low noise. By using this CCD image sensor as the image sensor, the sensor is able to scan at the required UV spectrum in order to improve the resolution. The use of such a sensor also increases the system throughput and permits the object to be inspected by both transmitted and reflected light at the same time. When using such an image sensor, the light source can be a laser, a flash lamp, or even a mercury arc lamp with a chopper or a modulator in order to produce short bright light flashes.

A number of embodiments are described below for purposes of example. According to one described embodiment, the reflected beams and transmitted beams are produced by separate light sources on opposite sides of the object. In a second described embodiment, they are produced by a common light source on one side of the object and optical steering elements, such as a flip-flop mirror, for alternatingly steering the light beam to the opposite sides of the object. In both of the above embodiments, the reflected beams and transmitted beams are sensed by a common image sensor.

A further embodiment is described wherein the reflected beams and transmitted beams are produced by a single light source on one side of the object, the reflected beams are sensed by a first sensor on one side of the object, and the transmitted beams are sensed by a second sensor on the opposite side of the object.

The invention also provides apparatus for optically inspecting an object in accordance with the above method.

BRIEF DESCRIPTION OF THE DRAWINGS

Further features and advantages of the invention will be apparent from the description below.

The invention is herein described, by way of example only, with reference to the accompanying drawings, wherein:

FIG. 4 is a timing diagram illustrating one example of timing of the electrical pulses producing the transmitted and reflected beams in the apparatus of FIG. 1;

FIG. 5 is a block diagram illustrating one manner of electrically processing the output of the image sensor;

DETAILED DESCRIPTION OF THE EMBODIMENTS

As indicated earlier, the method and apparatus of the present invention are particularly useful for optically inspecting photomasks in order to detect defects in both the clear areas and the opaque areas of the photomask.

Figure 1:
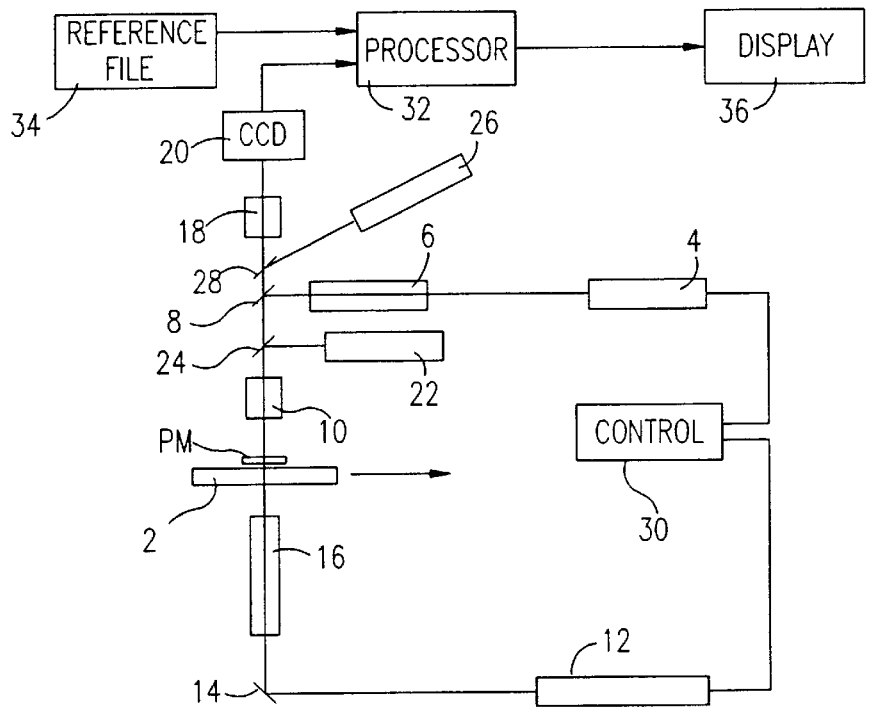
FIG. 1 is an optical diagram illustrating one form of apparatus constructed in accordance with the present invention.

The apparatus illustrated in FIG. 1 includes a stage 2 for receiving and transporting the photomask PM to be optically inspected. A first light source 4 located on one side of the photomask PM produces light flashes which are directed via an optical system 6, a beam splitter 8, and an objective lens 10, to one side of the photomask PM. A second light source 12 on the opposite side of the photomask PM produces light flashes directed by reflector 14 and optical system 16 to the opposite side of the photomask. The light from light source 4 is reflected from one face of photomask PM via a relay lens 18 to an area-type image sensor 20. The light from light source 12 is transmitted through the photomask PM, i.e., through both its faces, and through a relay lens 18 to the same image sensor 20 receiving the reflected light from light source 4.

The optical axis to the image sensor 20 further includes an autofocus device 22 controlling the objective lens 10 via a beam splitter 24, and a viewing eyepiece 26 receiving the image via a beam splitter 28 for viewing purposes.

The two light sources 4 and 12 are controlled by a control system, schematically indicated as 30, which periodically energizes or flashes the two light sources to cause each to generate a series of short-duration time-spaced light beams which are time-interlaced with each other. Thus, light source 4 produces a series of short-duration time-spaced light beams reflected from one face of the photomask PM; and light source 12 produces a series of short-duration time-spaced light beams which are transmitted through both faces of the photomask PM and which alternate with the reflected beams from light source 4. All the reflected beams from light source 4 and the transmitted beams from light source 12 are received by the common image sensor 20, which generates electrical outputs corresponding to the received reflected and transmitted beams.

The electrical outputs from image sensor 20 are fed to a processor 32 which processes them in comparison with reference data received by the processor from a reference data source 34. The reference data source could be stored in a database, or could be derived from another object or from another part of the same object being inspected. Processor 32 thus produces an indication of any discrepancies between the reference data and the data derived from the optical inspection of the photomask PM indicating defects in the photomask. The results of this processing are outputted to an output device, such as display 36.

Stage 2 receiving the photomask PM is an XY stage which continuously moves the photomask along the X-axis and/or Y-axis. The image sensor 20 is an area-type image sensor, preferably a two-dimensional matrix of CCDs (charge coupled devices). Such a sensor captures a full area image at one time even while the XY stage is moving the photomask PM at a constant velocity. In order to capture an unblurred image "on the fly" while the stage is moving the photomask PM, the CCD integration time should be short enough such that the captured image will not move too much during the image capture time. This requires that the integration time of the whole CCD shall be less or equal to the scanning time of one pixel.

Figure 2:
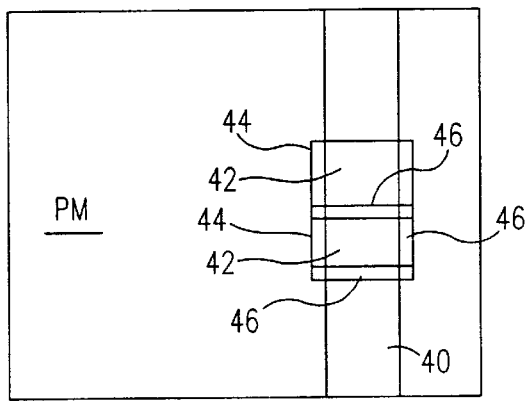
FIGS. 2 and 3 are diagrams illustrating the manner of optically inspecting a complete face of the object.

As shown in FIG. 2, the area of the photomask PM is inspected by slices. FIG. 2 illustrates one of the slices 40 extending vertically of the photomask PM. Each slice 40 is divided into rectangular areas 42 having a size equal to the area of the CCD image sensor 20 divided by the optical magnification of the imaging optics. As shown in FIG. 2, the rectangular area 42 of the respective slice 40 image at each shot is slightly smaller than the full area 44 covered by the CCD image sensor on the mask to produce a slight overlap 46 on each of the four sides. This assures obtaining a full mask image when combining the separate successive acquired images.

Figure 3:
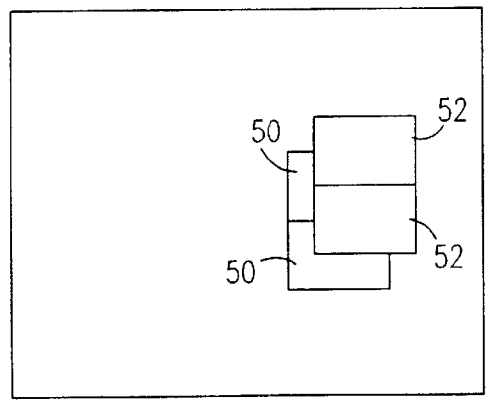

It will thus be seen that the CCD image sensor 20 receives two streams of images, namely the reflected images from light source 4, and the transmitted images from light source 12. Since the photomask PM is in continuous motion, there is thus a short delay between the two series of images received by the CCD image sensor. FIG. 3 illustrates this delay with respect to the horizontal shift for purposes of clarity, wherein it will be seen that the series of reflected images 50 are delayed with respect to the transmitted images 52 received by the CCD image sensor 20.

Preferably, each of the two light sources 4, 12, is pulsed for a period of less than 1 millisecond, more preferably, less than 100 microseconds, at a frequency of more than one MHz. This produces high-intensity light flashes of sufficiently short duration to avoid blurring of the images received by the CCD image sensor 20.

FIG. 4 illustrates the timing diagram of one example of operation of the system wherein each light source is pulsed for 60 microseconds and the pulses are spaced approximately 26 milliseconds during which the readout is performed by the image sensor. Assuming for example that the image sensor includes a matrix of 1K×1K pixels, the image sensor may be divided into two sections with the readout of each section operating at 20 MHz. Thus, the total throughput would be at 40 MHz. Higher data rates can be achieved by shorter pulses or wider sensors. For example, an 80 MHz data rate can be achieved by a 30 microsecond pulse or a 2K pixel-wide sensor.

It will be seen that the transmitted light flashes from light source 12 will cause a defect (e.g., a particle) on the clear area of the photomask to appear as a light fall-off, and a defect (e.g., hole) on the opaque area of the photomask to appear as a bright spot. The transmitted light flashes will not be able to locate a defect (e.g., particle) on the opaque area, but such a defect can be located by the reflected flashes from light source 4.

If a line-type CCD image sensor were used, the switching rate between the illumination modes would have to be within the line rate (e.g., about 20 KHz). However, by utilizing an area-type CCD image sensor as described above, the switching rate need be only within the frame rate (e.g., about 20 Hz) based on a data rate of 20 MHz and 1,000 pixels per line. This low rate of switching between the illumination modes is a particularly big advantage in the described system.

In this example, each integration time is approximately 60 microseconds during which the full field of view of 1K×1K of pixels of the image sensor 20 is illuminated by a short transmissive flash from light source 12 and is imaged by the imaging optics, including the objective lens 10 and relay lens 18, on the area image sensor 20.

As shown in FIG. 5, the image sensor produces two output streams 25a, 25b to two image processors 32a, 32b each operating at 20 MHz and outputting its contents to a serial combiner 33. After approximately 26 milliseconds (being equal to $1024^2/2 \times 20 \times 10^6$), the CCD image sensor is emptied and is ready for the next flash. Meanwhile, when the photomask, moving at constant velocity, reaches half the way to the next adjacent field of view of the transmitted light flashes from light source 12, a short light flash is generated by light source 4 to produce a reflected beam which illuminates a new 1K×1K pixels area, and its image is captured by image sensor 20 and removed through the two readouts 25a, 25b and image processors 31a, 32a to the result combiner 33. This procedure is repeated until the full mask area has been imaged twice, one with transmitted light flashes from light source 12, and the other with reflected light flashes from light source 4.

Preferably, the area-type CCD image sensor 20 is the cooled back-illumination CCD image sensor recently developed by the NASA Pluto program as briefly described above. This sensor has enhanced quantum efficiency in the UV spectral region, is capable of a very high data rate, and is characterized by very low noise. By using this CCD sensor as the image sensor 20, it is possible to scan at the required UV spectrum in order to improve the resolution. When this CCD image sensor is used as image sensor 20, the light sources can be pulsed lasers, flash lamps, or even mercury arc lamps. They can also include choppers or modulators in order to produce the short right light flashes.

Figure 6:
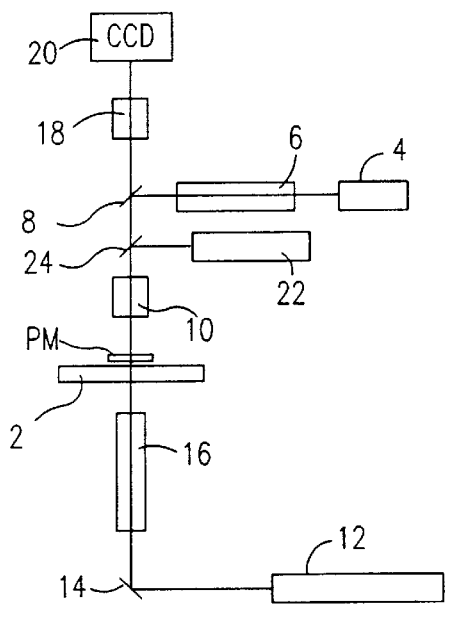
FIG. 6 is a diagram illustrating a modification in the apparatus of FIG. 1.

FIG. 6 illustrates an apparatus set up which is substantially the same as in FIG. 1, except that the eyepiece 26 and its beam splitter 28 are omitted.

Figure 7:
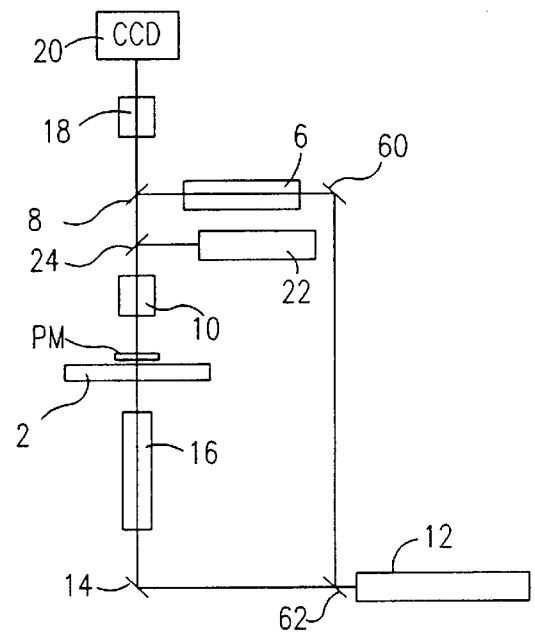
FIG. 7 is a diagram illustrating apparatus constructed in accordance with the present invention but using a single light source.

FIG. 7 illustrates another arrangement similar to that of FIG. 1. In addition to omitting the eyepiece 26 and its beam splitter 28, the arrangement illustrated in FIG. 7 includes a single light source 12 on the side of the photomask PM opposite to that of the image sensor 20. Instead of light source 4 on the same side of the photomask as the image sensor 20, the system of FIG. 2 includes a mirror 60 and a light-steering member 62, in the form of a flip-flop mirror, which alternately switches the light from light source 12 either to mirror 60 to produce the reflected light beams, or to mirror 14 to produce the transmitted light beams. In all other respects, the apparatus illustrated in FIG. 7 is constructed and operates in the same manner as described above with respect to FIG. 1.

Figure 8:
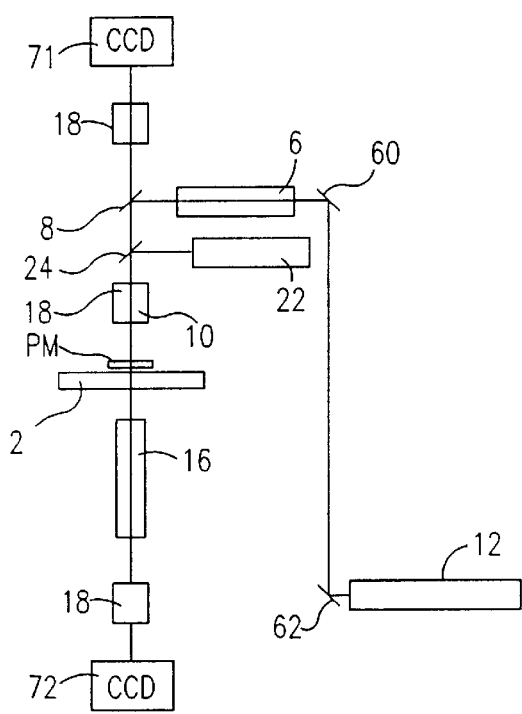
FIG. 8 is a diagram illustrating a further form of apparatus constructed in accordance with the present invention also using a single light source but two image sensors on opposite sides of the object.

FIG. 8 illustrates an apparatus similar to that of FIG. 7 including a single light source 12, but two area-type image sensors 71, 72. Thus, image sensor 71 is located on the same side as the photomask PM so as to receive the reflected beams from light source 70, and image sensor 72 is located on the opposite side of the photomask PM to receive the transmitted light beams from the light source. In all other respects, the structure and operation of the apparatus illustrated in FIG. 8 are the same as described above with respect to FIG. 7.

Figure 9:
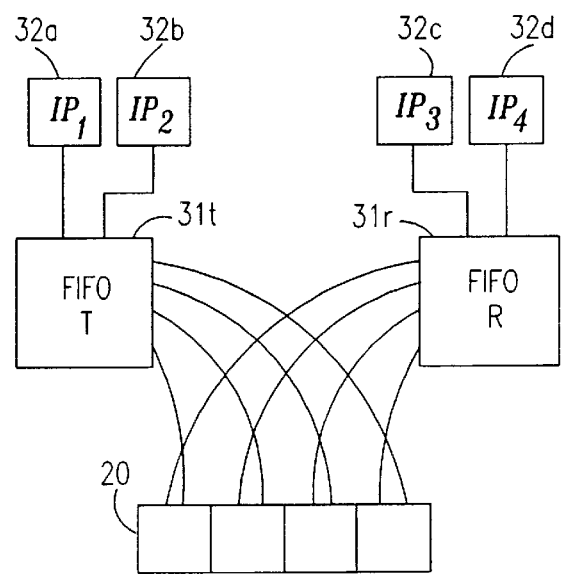
FIG. 9 is a block diagram illustrating a preferred arrangement for electrically processing the output of the image sensor.

FIG. 9 illustrates a preferred arrangement for processing the output of the image sensor 20 to enable relatively high throughput with processing circuitry operating at relatively lower speeds. For example, a transmissive and reflective inspection apparatus as described herein can be operated at an equivalent data rate of 40 MHz by using processing circuitry operating at 20 MHz, and a 1K×1K CCD image sensor according to the circuit illustrated in FIG. 1, as follows:

The CCD image sensor 20 is divided into four readout taps each operating at 20 MHz in order to transfer the fall 1K×1K. The transmissive flash first illuminates the object (photomask), the four taps of the CCD image sensor 20 transfer the transmissive data to a transmissive FIFO register 31t at the time the stage has moved one-half the distance, i.e., 512 lines. The FIFO register 31t receives the data at 80 MHz and transfers it to image processors $IP_1$ and $IP_2$ at 20 MHz each. At the time the stage reaches one-half the distance, i.e., line No. 512, the reflective flash illuminates the object (photomask), and the four taps of the CCD image sensor 20 will again transfer the data at total rate of 80 MHz but now to the reflective FIFO register 31r. This data is transferred to image processor $IP_3$ and $IP_4$ at 40 MHz.

In this manner, two quantities of 1K×1K pixels can be read out from the CCD image sensor at a data rate of 80 MHz each while operating the four pipe lines at a data rate of 20 MHz, two for the transmissive data and two for the reflective data. The image processing technique could be, for example, that described in U.S. patent application Ser. No. 07/801,761 or in U.S. patent application Ser. No. 07/880,100, both assigned to the same assignee as the present application.

While the invention has been described with respect to several preferred embodiments, involving the optical inspection of photomasks, it will be appreciated that the invention could also be used for optically inspecting other objects, such as printed circuit boards wherein the transmitted light flashes are used for detecting defects in plated through-holes or the like, as described for example in the above-cited Dotan et al. U.S. Pat. No. 5,216,479. Many other variations, modifications and applications of the invention will be apparent.

We claim:

1. A method of optically inspecting an object having upper and lower faces for indicating the condition of the object, comprising:

periodically reflecting a beam of light from one face of the object to produce a series of short-duration time-spaced reflected beams;

periodically transmitting a beam of light through the object including both faces thereof to produce a series of short-duration time-spaced transmitted beams time-interlaced with said reflected beams;

sensing said short-duration time-spaced reflected beams and transmitted beams, and generating electrical outputs corresponding thereto;

and processing said electrical outputs to provide an indication of the condition of said object.

2. The method according to claim 1, wherein said reflected beam and transmitted beams are sensed by an area-type image sensor.

3. The method according to claim 2, wherein said reflected beams and transmitted beams are produced by separate light sources on opposite sides of the object.

4. The method according to claim 3, wherein said reflected beams and transmitted beams are sensed by a common image sensor.

5. The method according to claim 2, wherein said reflected beams and transmitted beams are produced by a common light source on one side of the object, and optical steering elements alternatingly steering the light beam to the opposite sides of the object.

6. The method according to claim 3, wherein said reflected beams and transmitted beams are sensed by a common image sensor.

7. The method according to claim 2, wherein the step of generating electrical outputs comprises obtaining a plurality of signal outputs from a plurality of taps connected to said image sensor, and alternately sending said plurality of signal outputs to a transmissive data register and a reflective data register.

8. The method according to claim 1, wherein each of said reflected beams and transmitted beams is produced by a high intensity light source periodically energized for periods of less than 1 millisecond.

9. The method according to claim 8, wherein each of said reflected beams and transmitted beams is produced by a high intensity light source periodically energized for periods of less than 100 microseconds at a frequency of more than 1 MHz.

10. The method according to claim 9, wherein said high-intensity light source is a laser.

11. The method according to claim 8, wherein said high-intensity light source is a laser.

12. The method according to claim 1, wherein the object being optically inspected is a photomask having clear areas and opaque areas, and the condition to be indicated is the presence or absence of defects in said clear areas and opaque areas of the photomask.

13. Apparatus for optically inspecting an object having upper and lower faces for indicating the condition of the object, comprising:
a lighting system periodically reflecting a beam of light from one face of the object to produce a series of short-duration time-spaced reflected beams, and periodically transmitting a beam of light through both faces of the object to produce a series of short-duration time-spaced transmitted beams time-interlaced with said reflected beams;
a sensor sensing said short-duration time-spaced reflected beams and transmitted beams, and generating electrical outputs corresponding thereto;
and a processor receiving said electrical outputs and processing them to provide an indication of the condition of said object.

14. The apparatus according to claim 13, wherein said sensor comprises an area-type image sensor.

15. The apparatus according to claim 14, wherein said area-type image sensor includes a rectangular matrix of charge coupled devices (CCDs).

16. The apparatus according to claim 15, wherein said lighting system comprises first and second light sources on opposite sides of the object.

17. The apparatus according to claim 15, wherein said lighting system comprises:
a common light source on one side of the object producing short-duration time-spaced light beams;
a first optical system on said one side of the object;
a second optical system on the opposite side of the object;
and a light-beam steering device on said one side of the object periodically controlled to steer the light from said common light source alternatingly to said first optical system and to said second optical system.

18. The apparatus according to claim 17, wherein said light-beam steering device includes a flip-flop mirror.

19. The apparatus according to claim 15, wherein said lighting system comprises a single periodically-energized light source on one side of the object; and said sensor comprises a first sensor on said one side of the object for sensing the reflected beams, and a second sensor on the opposite side of the object for sensing the transmitted beams.

20. The apparatus according to claim 14, wherein said lighting system comprises first and second light sources on opposite sides of the object.

21. The apparatus according to claim 14, wherein said lighting system comprises:
a common light source on one side of the object producing short-duration time-spaced light beams;
a first optical system on said one side of the object;
a second optical system on the opposite side of the object;
and a light-beam steering device on said one side of the object periodically controlled to steer the light from said common light source altenatingly to said first optical system and to said second optical system.

22. The apparatus according to claim 14, further comprising a transmissive data register and a reflective data register, and wherein said sensor comprises a plurality of tabs, each coupled to said transmissive data register and reflective data register.

23. The apparatus according to claim 13, wherein said sensor is an area-type sensor sensing both said reflected beams and said transmitted beams.

24. The apparatus according to claim 13, wherein said lighting system is periodically energized to produce high-intensity beams of less than 1 millisecond duration.

25. The apparatus according to claim 24, wherein said lighting system is periodically energized to produce high-intensity beams of less than 100 microseconds duration at a frequency of more than 1 MHz.

26. The apparatus according to claim 13, wherein said lighting system includes a periodically energized laser.

27. A substrate defect inspection system, comprising:
a movable stage having support for the substrate;
a light source;
a source controller energizing the light source to generate light beam pulses;
optical elements arranged to receive and direct the light beam pulses onto said substrate;
a first detector positioned to detect light beam pulses reflected from the substrate; and,
a second detector positioned to detect light beam pulses transmitted through said substrate;
whereby the system provides simultaneously a picture produced from the light beam pulses reflected from the substrate and a picture produced from detect light beam pulses transmitted through said substrate.

28. The system of claim 27, further comprising a stage controller programmed to continuously move the stage while the source controller energizes the light source.

29. A substrate defect inspection system, comprising:
a movable stage having support for the substrate;
a light source;
a source controller energizing the light source to generate light beam pulses;
optical elements arranged to receive the light beam pulses and direct some of the light beam pulses onto a first surface of said substrate and the remaining light beam pulses onto a second surface of said substrate;
a light detector positioned to detect light beam pulses reflected from the first surface of the substrate and light beam pulses transmitted through said first and second surfaces of the substrate;
whereby the system provides a picture produced from the light beam pulses reflected from the substrate and a picture produced from detect light beam pulses transmitted through said substrate.

30. The system of claim 29, wherein the optical elements direct light beam pulses onto the first and second surfaces of said substrate in an interlaced manner.

31. The system of claim 30, further comprising a stage controller programmed to continuously move the stage while the source controller energizes the light source.

32. A substrate defect inspection system, comprising:

a movable stage having support for the substrate;

a first light source;

a second light source;

a source controller energizing the first and second light sources to generate light beam pulses, the light beam pulses from the first light source interlacing with the light beam pulses from the second light source;

a first set of optical elements arranged to receive and direct the light beam pulses from the first light source onto a first surface of said substrate;

a second set of optical elements arranged to receive and direct the light beam pulses from the second light source onto a second surface of said substrate;

a light detector positioned to detect light beam pulses reflected from the first surface of the substrate and light beam pulses transmitted through said first and second surfaces of the substrate;

whereby the system provides substantially simultaneously a picture produced from the light beam pulses reflected from the substrate and a picture produced from detect light beam pulses transmitted through said substrate.

* * * * *